United States Patent
Bardy et al.

(10) Patent No.: US 6,269,267 B1
(45) Date of Patent: Jul. 31, 2001

(54) CONFIGURABLE ARRHYTHMIA ANALYSIS ALGORITHM WITH SECURITY INTERFACE

(75) Inventors: Gust H. Bardy, Seattle; Thomas D. Lyster, Bothell, both of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/547,785

(22) Filed: Apr. 12, 2000

Related U.S. Application Data (63) Continuation of application No. 09/146,059, filed on Sep. 2, 1998, now Pat. No. 6,108,578.

(51) Int. Cl.$^7$ .................................................. A61N 1/39
(52) U.S. Cl. ...................................... 607/5; 607/7
(58) Field of Search ............................................. 607/5, 7

(56) References Cited

U.S. PATENT DOCUMENTS

| | | |
|---|---|---|
| 4,523,595 | 6/1985 | Zibell . |
| 4,919,144 | 4/1990 | Vandehey . |
| 5,014,697 | 5/1991 | Pless et al. . |
| 5,342,403 | 8/1994 | Powers et al. . |
| 5,366,486 | 11/1994 | Zipes et al. . |
| 5,474,574 | 12/1995 | Payne et al. ............................ 607/7 |
| 5,549,115 | 8/1996 | Morgan et al. . |
| 5,591,213 | 1/1997 | Morgan . |
| 5,593,426 | 1/1997 | Morgan et al. . |
| 5,601,612 | 2/1997 | Gliner et al. . |
| 5,607,454 | 3/1997 | Cameron et al. . |
| 5,611,815 | 3/1997 | Cole et al. . |
| 5,620,471 | 4/1997 | Duncan . |
| 5,662,690 | 9/1997 | Cole et al. . |
| 5,716,380 | 2/1998 | Yerkovich et al. . |
| 5,725,559 | * 3/1998 | Alt et al. .................................. 607/5 |
| 5,782,878 | 7/1998 | Morgan et al. . |
| 5,879,374 | 3/1999 | Powers et al. . |
| 5,891,170 | 4/1999 | Nitzsche et al. . |
| 6,021,349 | * 2/2000 | Arand et al. ............................ 607/5 |
| 6,088,616 | * 7/2000 | Olson et al. ............................ 607/5 |

FOREIGN PATENT DOCUMENTS

| | | |
|---|---|---|
| 0555590A2 | 12/1992 | (EP) . |
| 756878A3 | 7/1996 | (EP) . |
| WO95/22372 | 1/1995 | (WO) . |
| WO98/44988 | 4/1998 | (WO) . |

\* cited by examiner

Primary Examiner—Carl H. Layno

(57) ABSTRACT

An electrotherapy device includes a power supply and electrodes. The electrodes are coupled to the power supply to deliver a defibrillating shock to a patient. Electronic circuitry is coupled to the electrodes and is operable to detect heart rhythms via the electrodes. Further, control circuitry is coupled to the electronic circuitry and the power supply and configurable to selectively classify patient heart rhythms that generate a shockable condition, the control circuitry operable to arm the power supply for energizing the electrodes responsive to such detectable shockable condition. A method is also provided.

34 Claims, 7 Drawing Sheets

TABLE 1: ENABLE FUNCTIONALITY GENERATED BY THREE DIFFERENT CLASSIFIER CONFIGURATIONS CORRESPONDING TO THREE DIFFERENT CLASSES OF OPERATORS

| ENABLE SHOCK | X |
|---|---|
| DISABLE SHOCK | O |

DETECTED HEART RHYTHM

| CLASSIFIER CONFIGURATION | CLEAR VF | MONOMORPHIC VT | LOW AMPLITUDE VF/ASYSTOLE | NORMAL SINUS |
|---|---|---|---|---|
| A. WELL TRAINED OPERATOR | X | X | X | O |
| B. MODERATELY TRAINED OPERATOR | X | X | O | O |
| C. MINIMALLY TRAINED OPERATOR | X | O | O | O |

FIG. 7

CONFIGURABLE ARRHYTHMIA ANALYSIS ALGORITHM WITH SECURITY INTERFACE

CROSS REFERENCE TO RELATED APPLICATION

This is a continuation of application Ser. No. 09/146,059 filed on Sep. 2, 1998, now U.S. Pat. No. 6,108,578.

FIELD OF THE INVENTION

The invention relates to an electrotherapy apparatus and method for delivering an electrical pulse to a patient's heart. This invention also relates to an apparatus and method for selectively configuring an electrotherapy apparatus by adjusting criteria used to determine shock and no-shock conditions based upon categories of detected heart rhythms such that a level of operator judgment is enabled commensurate with the skill level of an intended operator.

BACKGROUND OF THE INVENTION

A frequent consequence of heart attacks is the development of cardiac arrest associated with a heart arrhythmia, such as ventricular fibrillation. Electrotherapy can be performed by delivering an electrical pulse to a patient's heart in order to treat ventricular fibrillation. More particularly, ventricular fibrillation may be treated by applying an electric shock to the patient's heart through the use of a defibrillator. The chances of surviving a heart attack decrease with time after the attack. Quick response to a heart attack by administration of a defibrillating shock as soon as possible after the onset of ventricular fibrillation is therefore often critically important.

In order to be effective, a defibrillation shock must be delivered to a patient within minutes of the onset of ventricular fibrillation. Studies have shown that defibrillation shocks delivered within one minute after ventricular fibrillation may approach up to 100% survival rate. The survival rate falls to approximately 30% if six minutes have elapsed before the shock is administered. Beyond twelve minutes, the survival rate approaches zero.

One way of decreasing the time required to deliver a defibrillation shock to a patient is to greatly increase the availability of defibrillators in proximity with potential patients. Recently, the development of lightweight, relatively low-cost defibrillators has enhanced availability and contributed to decreasing the response time for patients needing treatment. More particularly, low-cost lightweight defibrillators manufactured by Heartstream, Inc. of Seattle, Wash., utilize an impedance-compensating biphasic waveform which has reduced size and cost, thereby increasing the availability of such devices to persons in outside-of-hospital settings. For example, such defibrillators have been deployed on first-response vehicles and to locations where large groups of individuals are gathered, such as in office buildings, corporate campuses, airplanes, health clubs, stadiums, and theaters. Such deployment to many environments contributes to greatly shortening the time from a patient's collapse to the delivery of a first shock.

With greatly increased deployment of such portable external defibrillators, the response time to shock a patient is being greatly reduced. However, an expanded first-response force needs to be trained so as to include a broad range of physician-authorized personnel, such as fire service and ambulance personnel, police officers, flight attendants, security guards, safety officers, and any other health care professional or appropriately trained individual with a duty to respond. Presently, such attempts are being undertaken.

One problem associated with expanding the use of defibrillators to physician-authorized personnel has been the varying degrees of training and skill that such personnel possess. Depending upon the environment in which an external defibrillator is employed, it might be desirable to control the functionality of such defibrillator so that it is tailored to match the level of skill and training that an intended operator possesses. Only through a dramatic improvement in defibrillator access, accompanied by appropriate training and delivered functionality, will sudden cardiac arrest lose its distinction as one of the nation's leading killers.

Prior art electrotherapy devices are known for producing electric shock to treat patients for a variety of heart arrhythmias. For example, manual external defibrillators provide relatively high-level shocks to a patient, usually through electrodes attached to the patient's torso, to convert ventricular fibrillation to a normal sinus rhythm. Similarly, external cardioverters, which are also manual defibrillators, can be used to provide shocks to convert atrial fibrillation to a more normal heart rhythm. Manual defibrillators require a significant amount of training, whereas automatic defibrillators tend to be expensive and invasive. One type of defibrillator is an implantable defibrillator which is relatively expensive, invasive, and requires a reduced level of shock delivery because of a direct current path to a patient's heart. Another type of defibrillator is an automatic external defibrillator (AED) which automatically analyzes patient heart rhythms and delivers electrotherapeutic pulses to a patient's heart indirectly, through the patient's skin and rib cage. Hence, external defibrillators tend to operate at higher energies, voltages, and/or currents.

Hardware and/or software electrocardiogram (ECG) analysis devices and analysis implementations are known within prior art defibrillators, both implantable and external, for detecting heart function so as to characterize a patient's heart condition. Furthermore, such prior art defibrillators are known for generating defibrillator waveforms that are characterized according to the shape, polarity, duration, and number of pulse phases. Typically, such heart function detection and defibrillator waveform generation are carried out via an ECG arrhythmia analysis algorithm and a discharge controller having discharge circuitry, respectively.

One approach for detecting patient heart function is shown in U.S. Pat. No. 5,014,697 to Pless, et al. (incorporated herein by reference). The Pless, et al, patent discloses a two-channel defibrillator having a programmable stimulator. The stimulator provides an assessment of lethal ventricular tachyarrhythmias in determining defibrillation thresholds during implantable defibrillator procedures. An initial test defibrillation shock is delivered to a patient, after which an automatic charging circuit and dual-channel, high-voltage capacitor circuits operate to reduce the time in which a rescue shock can be delivered to a patient. A microprocessor-controlled display system includes an operator interface that provides information parameters regarding the defibrillation shocks being delivered.

Another approach for detecting patient heart function is shown in U.S. Pat. No. 5,620,471 to Duncan (incorporated herein by reference). The Duncan patent discloses an apparatus for applying atrial and ventricular therapies to a patient's heart using an implanted cardiac stimulating device. Atrial and ventricular heart rates are monitored with the device to determine whether the patient is suffering from atrial or ventricular arrhythmia, and to then determine what type of therapy is appropriate for application to the patient's heart. Atrial and ventricular heart rates are compared via an algorithm to determine if the ventricular heart rate exceeds the atrial heart rate and to determine whether the ventricular heart rate is stable. According to one implementation, an early atrial stimulation pulse can also be applied to determine whether the ventricular heart rate follows the atrial heart rate. Therapy is applied to the patient's heart based upon determinations between atrial and ventricular heart rates.

Yet another approach to monitoring and defibrillating a patient's heart is provided by U.S. Pat. No. 5,474,574 to Payne, et al. (incorporated herein by reference). The Payne, et al., patent discloses a cardiac monitoring and defibrillation system configurable as a bedside or an ambulatory unit. Amplification and processing circuitry receives and conditions inputs from sensing apparatus such as electrocardiograms, blood oxygenation sensors, blood pressure monitors, and a cardiac acoustical transducer. Noise and artifact discrimination is implemented to prevent erroneous detection of the onset of cardiac arrhythmias. In response to condition inputs from the monitoring apparatus, a microprocessor controls therapeutic electrical stimulation being delivered to a patient according to a cardioverter/ defibrillator step therapy method. A control panel or external programming and monitoring unit can be utilized to program and control the microprocessor. According to one construction, the system includes a bidirectional communication link which allows monitoring and programming of the microprocessor by a physician at a remote location. Additionally, the system provides a method for detecting cardiac arrhythmias and distinguishing between the different types of arrhythmias which may be detected.

One approach for generating and delivering a relatively low-energy multiphasic waveform to a patient is shown in U.S. Pat. No. 5,601,612 to Gliner, et al. (incorporated herein by reference). The Gliner, et al., patent discloses an external defibrillator that automatically compensates for patient-to-patient impedance differences in the delivery of electrotherapeutic pulses for defibrillation and cardioversion. An energy source is discharged through electrodes to the patient to provide a biphasic voltage or current pulse. The delivered biphasic pulse can be altered to compensate for patient impedance differences by changing the nature of the delivered electrotherapeutic pulse, resulting in a smaller, more efficient and less expensive defibrillator.

Other electrotherapy apparatus and methods are shown in Cole, et al., U.S. Pat. No. 5,662,690; Morgan, et al., U.S. Pat. No. 5,549,115; Morgan, et al., U.S. Pat. No. 5,593,426; Morgan, U.S. Pat. No. 5,591,213; and Cole, et al., U.S. Pat. No. 5,611,815, all of which are incorporated herein by reference.

Prior art defibrillators have addressed the problem of detecting a heart condition requiring electrotherapy, and delivering a corresponding therapeutic shock pulse to a patient. However, the deployment of portable external defibrillators to a variety of new settings or deployment environments has placed such devices in the hands of less skilled operators. For example, the placement of such devices on airplanes has provided great benefits in reducing the time before delivery of a first shock. However, the operators of such devices are generally less skilled than operators in the past, even for cases where they are given some degree of training. Accordingly, the placement of such defibrillators into a greater variety of environments subjects the devices to use by a greater variety of personnel having different degrees of skill and training.

Furthermore, providing defibrillators to a wider range of patients, including children and infants, is a natural extension to a goal of providing wider and more rapid access to defibrillators.

Therefore, in an effort to optimize the performance of such devices within a specific environment, it becomes necessary for a manufacturer to tailor operation and functionality of a specific device for an intended user or operator and/or patient. Where the skill level and training of an intended user is well known, an electrocardiogram (ECG) signal analyzer can be designed for an automated defibrillator having a specific combination of functional trade-offs that optimize performance for that intended user. Additionally, there exists a further need to configure a defibrillator for use with different patients.

For example, the placement of such a defibrillator into the hands of a highly-skilled and highly-trained paramedic or physician enables a manufacturer to optimize sensitivity of the ECG signal analyzer, and to impart specificity within the analyzer which enables the operator to make final judgments on whether a patient needs to be shocked. Accordingly, such highly-skilled and highly-trained operators can be provided with additional information about a patient's heart function and condition which enables such highly-skilled and highly-trained operators to make judgment calls based upon whether a patient should be shocked.

On the other hand, if an intended operator is minimally trained and has a minimal skill level, a manufacturer must design a separate ECG signal analyzer for use within the automated defibrillator. A modified arrhythmia analysis algorithm may be employed. Furthermore, hardware changes might also be required in order to deliver a defibrillator that is best suited for use by a low skill and/or minimally trained operator. For example, where a minimally trained operator such as a flight attendant is the likely operator of a defibrillator, it may be appropriate to emphasize specificity over sensitivity, not enabling a significant degree of operator judgment to be exercised in deciding whether a patient is to be shocked. If the AED is used on small children, it may be required to employ an Algorithm Analysis (AA) match to the pediatric electrocardiogram (ECG).

Current prior art defibrillators contain ECG signal analyzers having an arrhythmia analysis implementation (hardware and/or software) which incorporates a fixed set of assumptions and trade-offs, giving no capacity to adapt functionality of the defibrillator to the skill level of the intended operator. Therefore, a manufacturer must design specific and distinct defibrillator devices that are tailored for each specific use for an intended operator having a predefined skill level or training. Hence, it becomes necessary for a manufacturer or distributor of such products to maintain a number of different models of defibrillators which are specifically designed to deliver functionality that matches the training and skill level of the intended operator encountered in the deployment environment.

Accordingly, it is likely that a defibrillator designed for use with a low-skilled and little-trained operator will find its way into the hands of an operator in a deployment environment who is highly skilled and highly trained. Such a device will be designed to prevent an operator from making personal judgment calls on whether to deliver a shock to a patient. Hence, a highly-skilled operator will be prevented from making judgment calls on whether or not a patient should be shocked. Such judgment calls become particularly important when dealing with borderline heart rhythms which might be suitable for shocking. Similarly, a defibrillator having an ECG arrhythmia analysis implementation suited for a highly-skilled and highly-trained operator might find its way into the hands of a low-skilled and little-trained operator. A similar, but more complicated, problem occurs here wherein a low-skilled operator is enabled with the power to use operator judgment and potentially apply a shock treatment to a patient having a borderline rhythm group which should not be shocked. A problem may occur if an adult AED is applied to a child, and vice versa.

Hence, a significant problem occurs in that the placement of such environment-specific defibrillator devices might be mis-matched with the operator and/or patient. For the case where a device is sold to an organization, it is likely that they might change the environment in which such device is being utilized. For example, a device that is configured for use with a highly-trained and highly-skilled operator might later be deployed in an environment where a low-skilled and little-trained operator has the device for use. Such occurrence is extremely likely to happen in the event that an organization has already paid for the device, and is faced with having to expend further monies to purchase a device that is reconfigured for an operator having a different skill level.

Therefore, there is a need to provide for a single, common defibrillation device having an ECG arrhythmia analysis apparatus capable of being configured/reconfigured so as to enable deployment/re-deployment for operators having varying degrees of training and skill level or varying patient characteristics. Therefore, it would be desirable to obtain improvements in automated defibrillators that enable the manufacture and assembly of a single, common defibrillator having ECG arrhythmia analysis features capable of being selectively tailored. It would further be desirable to provide a method for reconfiguring such an automated defibrillator to impart a desired degree of functionality to an operator.

SUMMARY OF THE INVENTION

The invention provides an apparatus and a method for configuring electrocardiogram (ECG) arrhythmia analysis features within an automated defibrillator. A configurable arrhythmia analysis algorithm is implemented within a processor and circuitry of an automated defibrillator with an analysis design having the capability to distinguish between definite shockable heart rhythms, definite non-shockable heart rhythms, and a variety of borderline heart rhythms which are not clearly shockable or non-shockable. The algorithm is designed with a standard set of electrocardiogram (ECG) measures, and includes a classifier which combines such standard set of measures to produce a single shock/no-shock decision that arms/disarms the device. Various configurations of the algorithm match specific requirements for delivering functionality desired for an intended operator found within a deployed location in order to achieve pre-selected functionality. Specific configurations of the algorithm are achieved by modifying parameters of the classifier, which uses the same set of standard ECG measures that are used for present prior art electrocardiogram devices.

According to one aspect of the invention, an electrotherapy device includes a power supply and electrodes. The electrodes are coupled to the power supply to deliver a defibrillating shock to a patient. Electronic circuitry is coupled to the electrodes and is operable to detect heart rhythms via the electrodes. Further, control circuitry is coupled to the electronic circuitry and the power supply and configurable to selectively classify patient heart rhythms that generate a shockable condition, the control circuitry operable to arm the power supply for energizing the electrodes responsive to detection of shockable condition patient heart rhythms.

According to another aspect of the invention, an electrotherapy device includes a power supply and electrodes. The electrodes are coupled to the power supply and operative to monitor a patient's heart rhythms and deliver a defibrillating shock to a patient. Also included in the electrotherapy device is ECG circuitry coupled to the electrodes, and operative to detect patient heart rhythms and generate measured parameter values indicative of a patient heart rhythm. A controller is coupled to the ECG circuitry and the power supply and is operative to enable shock delivery to a patient via the power supply responsive to the measured parameter values indicative of a detected patient heart rhythm. Further, a classifier is associated with the controller and is operative to associate a pre-selected set of parameters, each parameter having a predetermined range of values, to generate a shock/no-shock decision.

Another aspect of the invention is an electrotherapy device which includes a power supply and electrodes which are coupled to the power supply. Electronic circuitry is coupled to the power supply and is operable to monitor electrocardiographic (ECG) data signals, and is adapted to deliver a defibrillation shock to a user's body. A reconfigurable classifier is coupled to the electronic circuitry and the power supply and is operative to associate a pre-selected set of parameters, each parameter characterizing the ECG data signals, to generate a shock/no-shock decision. Yet another aspect of the invention is a method for optimizing shock delivery from a defibrillator to a patient which defines parameters that characterize heart function and accesses control circuitry. The control circuitry is operative to implement a classifier defined by at least one of the parameters, the classifier operative to enable delivery of shock to a patient based upon detected values of at least one of the parameters relative to predetermined values of the at least one parameter. The classifier is optimized by adjusting at least one of: (a) the contribution of one or more of the parameters used to implement the classifier; (b) the predetermined values of one or more of the parameters used to implement the classifier that enables shock delivery; and (c) the relative contribution of one parameter relative to other parameters to enable shock delivery.

Objects, features and advantages of this invention are to provide a relatively low-cost, lightweight external defibrillator which substantially reduces the need to manufacture a number of different versions intended for deployment in different environments and usable by operators having a variety of different potential skill levels and training, is quickly and easily reconfigurable by an authorized control person, is quickly and easily assembled and repaired, reduces the number of parts required to manufacture a variety of differently configured devices, and is rugged, durable, and of economical manufacture and assembly.

DESCRIPTION OF THE DRAWINGS

FIG. 4 is an exploded perspective view taken from the top side of the defibrillator of FIG. 3;

DETAILED DESCRIPTION OF THE INVENTION

Figure 1:
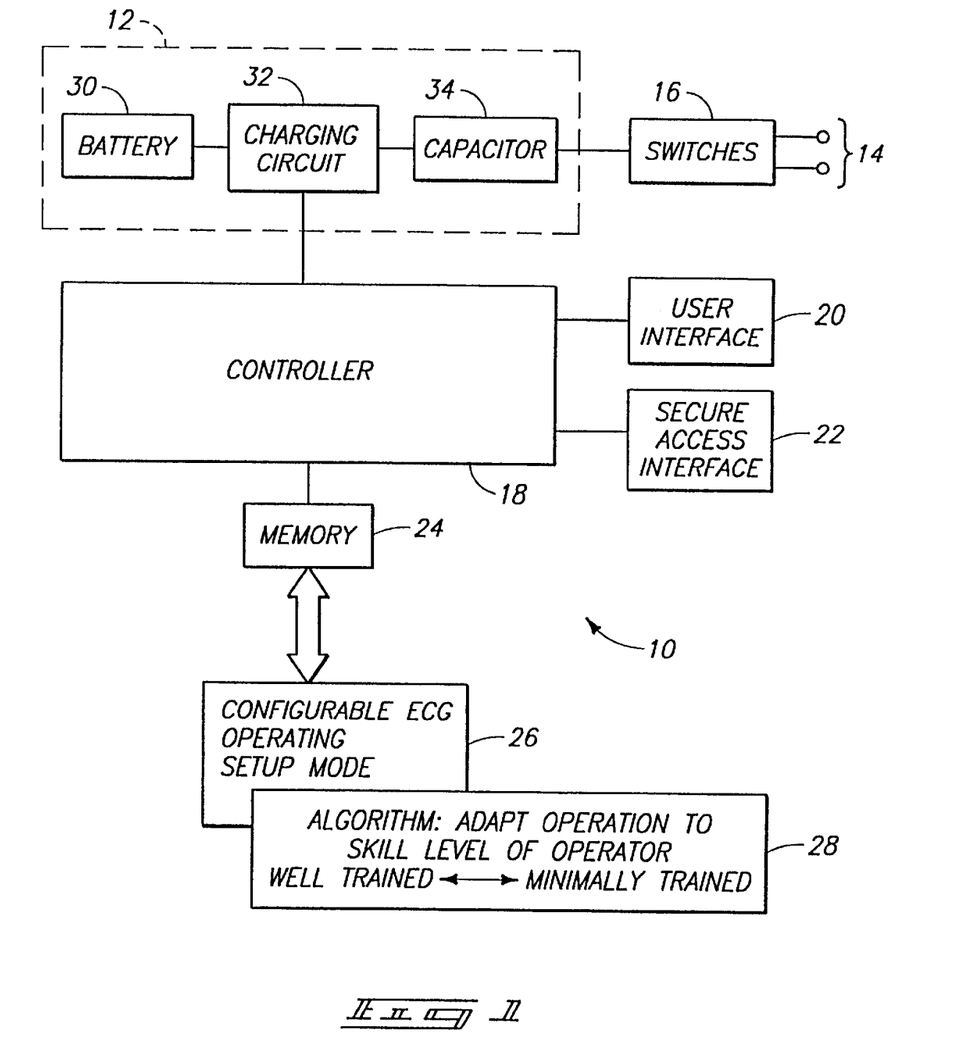
FIG. 1 is a schematic block diagram of a defibrillator system having a configurable electrocardiogram (ECG) arrhythmia analysis algorithm according to a preferred embodiment of this invention.

FIG. 1 illustrates an electrotherapy system according to a preferred embodiment of this invention. This system is configured as a defibrillator 10 that incorporates electrocardiogram (ECG) features. Defibrillator 10 is configured as an external defibrillator capable of delivering an optimizable biphasic waveform for treating a particular kind of heart arrhythmia. According to well-known details within the prior art, patient-to-patient differences are taken into account when delivering an optimal biphasic waveform to a patient. Details of one such implementation are disclosed in Cameron, et al., U.S. Pat. No. 5,607,454 (already incorporated by reference). Likewise, prior art techniques for detecting a heart rhythm and determining whether a shock needs to be delivered are also incorporated into defibrillator 10 according to prior art techniques for configuring a specific electrocardiogram (ECG) system within a defibrillator.

According to FIG. 1, defibrillator 10 is a semi-automatic defibrillator. Optionally, defibrillator 10 may be automatic, or manual (where secured access is provided by a physical lock and key or a software key) to enable a highly-skilled operator to bypass restricted functionality features when utilizing the invention. Defibrillator 10 has an energy source 12, electrode connectors 14, and switches 16 interposed between the energy source and the electrode connectors. Energy source 12 may be made up of any energy storage medium such as a battery, a capacitor, or a capacitor bank, and a charging circuit.

A controller 18 is provided within defibrillator 10 for controlling the operation of energy source 12 and switches 16. According to one implementation, controller 18 comprises a microprocessor. Controller 18 controls delivery of an electrical pulse to electrode connectors 14, and receives inputs through a user interface 20. One form of user interface 20 comprises a user input such as one or more activation buttons or actuators, one or more digital or analog ports, or combinations thereof. Controller 18 is also operative to send out information through an output of user interface 20 which may include a display, digital or analog ports, or combinations thereof. For the case where defibrillator 10 is automatic or semi-automatic, controller 18 includes an electrocardiogram (ECG) signal analyzer according to any of a number of constructions well understood in the art.

Defibrillator 10 also includes a secure access interface 22 operative to enable restricted access by a manufacturer or medical personnel to enable configuration/reconfiguration of defibrillator 10 to adjust the sensitivity and specificity of the electrocardiogram signal analyzer. In one form the signal analyzer comprises an ECG arrhythmia analysis algorithm. Secure access interface 22 may comprise one or more buttons or other actuators, one or more digital or analog ports, or combinations thereof, or a switch contained/hidden within a housing in a location inaccessible by a user. Furthermore, secure access interface 22 may include a display, digital or analog ports, or combinations thereof. Furthermore, defibrillator 10 also has a memory 24 for storing digital and/or analog information.

Defibrillator 10 may be used to deliver an electrical pulse or shock to a patient in response to a need that is detected by the corresponding ECG signal analyzer. For example, if defibrillator 10 is a semi-automatic defibrillator, it may be used as follows: First, the user attaches electrodes at one end to electrode connectors 14 and at an opposite end to a patient. The ECG signal analyzer of defibrillator 10 is implemented via controller 18, principally as software. Such ECG signal analyzer analyzes the ECG signals of the patient which are obtained through the electrodes to determine whether it is advisable to deliver a shock to a patient. Defibrillator 10 then displays a shock/no-shock advice to an operator via user interface 20. If a shock is advised and the user/operator decides to deliver a shock, then the user may actuate controller 18 through user interface 20 in order to deliver a shock to a patient. Such shock is delivered through the electrodes that are already affixed to the patient.

In order to configure defibrillator 10 for optimized use by an operator within a deployment environment, a configurable electrocardiogram (ECG) operating set-up mode 26 is implemented on defibrillator 10. More particularly, operating set-up mode 26 is stored within memory 24 and implemented via controller 18. In this manner, configurable operating set-up mode 26 can be configured/reconfigured via secured access at a medical control station by way of a secure access interface 22. Accordingly, a control group of personnel who have security access may reconfigure operating set-up 26 by way of an operating algorithm 28 which enables the secured access personnel to adapt operation of defibrillator 10 to a known skill level for an operator. For example, a manufacturer can configure/reconfigure defibrillator 10 within the assembly plant.

Accordingly, defibrillator 10 can be reconfigured such that controller 18 makes shock/no-shock recommendations which account for the skill level and training of the operator who is situated to utilize the defibrillator. Hence, the ECG analyzer of defibrillator 10 can be configured/reconfigured to optimize its operation based upon the training and skill level of an actual operator that is expected to utilize the defibrillator within a specific deployment environment. Accordingly, trade-offs are significantly influenced by assumptions that are made about the training and skill level of the intended operator. Such trade-offs enable optimization between sensitivity and specificity within algorithm 28, enabling reconfiguration of operating set-up mode 26 to best deliver functionality to a patient via the actual operator. Defibrillator 10 can be configured/reconfigured based upon the training that operators/users have had which enables the deployment of defibrillator 10 within a broad range of environments where the range of training and skill for operators can widely vary.

Accordingly, a manufacturer can construct defibrillator 10 from a single, common construction wherein hardware and software is implemented in nearly an identical manner. However, a secure operator or the manufacturer is capable of reconfiguring operating set-up mode 26 so as to tailor functionality of defibrillator 10 to best match the skill level of the operator most likely to utilize defibrillator 10 within a specific deployment environment. Additionally, functionality of defibrillator 10 can be reconfigured to best match a patient.

For example, defibrillator 10 can be reconfigured to match a patient by providing an electrode connector that is encoded to receive a specific electrode. More particularly, an encoded electrode connector can be provided for receiving an adult electrode and a pediatric electrode, wherein receipt of a pediatric electrode within the encoded electrode connector causes control circuitry to reconfigure the defibrillator 10 to deliver a shock best suited for a pediatric patient.

According to another example, where the deployment environment is likely to place defibrillator 10 within the hands of a highly-skilled operator having a significant amount of training (for example, a paramedic or a physician), it is likely that a high level of decision-making capability be imparted to the operator such that the operator can make decisions on whether or not to actuate defibrillator 10 to deliver a shock to a particular patient. For example, if the patient is unconscious and a borderline rhythm is detected by defibrillator 10, a highly-skilled operator may make a decision to deliver a shock. For example, a highly-skilled operator may decide that an unconscious patient is capable of receiving a shock when a monomorphic VT rhythm has been detected. Similarly, such a shock may be warranted where a low amplitude VF/asystole rhythm has been detected. However, it may be undesirable to enable such functionality where the operator is lower skilled or has less training. For example, deployment of the same defibrillator into the hands of a moderately-skilled or low-skilled operator might warrant the disablement of such features for enabling shock delivery during borderline rhythm detection. Hence, the deployment of defibrillator 10 into the hands of a flight attendant might warrant disablement of shock delivery when monomorphic VT and low amplitude VF/asystole rhythms are detected. Accordingly, a single, common defibrillator 10 can be constructed for use in various deployment environments. Such single, common defibrillator 10 is imparted with secure access features that enable selective configuration for an intended deployment environment by operators having a pre-defined level of skill and training.

Accordingly, defibrillator 10 of this invention may be configured for operation within any one of a number of different deployment environments, each subjecting defibrillator 10 to use by operators having a known level of skill and training. In this manner, high levels of functionality can be imparted to defibrillator 10 for use by highly-skilled operators wherein sensitivity is emphasized over specificity, trusting the operator to make final judgments as to the need to shock a patient. Similarly, where an operator is assumed to be minimally trained, it is appropriate to emphasize specificity over sensitivity, not depending much on operator judgment.

Prior art ECG algorithms incorporate a fixed set of assumptions and trade-offs, and there exists no capacity to adapt/reconfigure a defibrillator to the skill level of an operator. Accordingly, implementation of Applicant's invention permits an arrhythmia analysis algorithm and hardware to be configured/reconfigured in a set-up mode by an authorized person such that the resulting defibrillator more closely delivers functionality commensurate with the skill level of the operator who will use the defibrillator within a specific deployment environment.

Additional features implemented by Applicant's invention entail reconfiguring defibrillator 10 by reconfiguring a user interface of defibrillator 10. Similarly, defibrillator 10 can be reconfigured with different protocols. For example, different groupings of protocol parameters consist of setting a pre-defined set of parameters according to specific defibrillation guidelines such as those defined by the American Heart Association (AHA). The ability to reconfigure protocol parameters or enable reconfiguration of defibrillator 10 between pre-set groups of protocol parameters is envisioned with Applicant's invention. One such group of protocol parameters might correspond with an American Heart Association (AHA) requirement. Another set of protocol parameters might correspond with a European Resuscitation Council (ERC) group of protocol parameters. The notion of forming groups of protocol parameters and the notion of grouping arrhythmia analysis algorithm parameters enables reconfiguration of defibrillator 10 to achieve the best functionality for an intended environment based upon selection of protocol parameters and/or algorithm parameters within a group of pre-defined parameters.

As shown in FIG. 1, energy source 12 comprises an energy storage medium 30 such as a battery, a charging circuit 32, and a capacitor or capacitor bank 34 that forms an energy source, analysis system and electrodes. It is understood that energy source 12 comprises a high-voltage (HV) delivery device or power supply capable of storing sufficient energy to deliver a defibrillating shock to a patient through electrodes 140 (see FIG. 2).

A suitable defibrillator having additional functionality and structural features for use with this invention is disclosed in U.S. patent application Ser. No. 08/227,553, "Electrotherapy Method and Apparatus", filed Apr. 14, 1994, and U.S. patent application Ser. No. 08/240,272, "Defibrillator With Self-Test Features", filed May 10, 1994. The disclosures of such patent applications are herein incorporated by reference. The following exemplary details disclose use of this invention with an external defibrillator having operating features described in such two patent applications.

Figure 2:
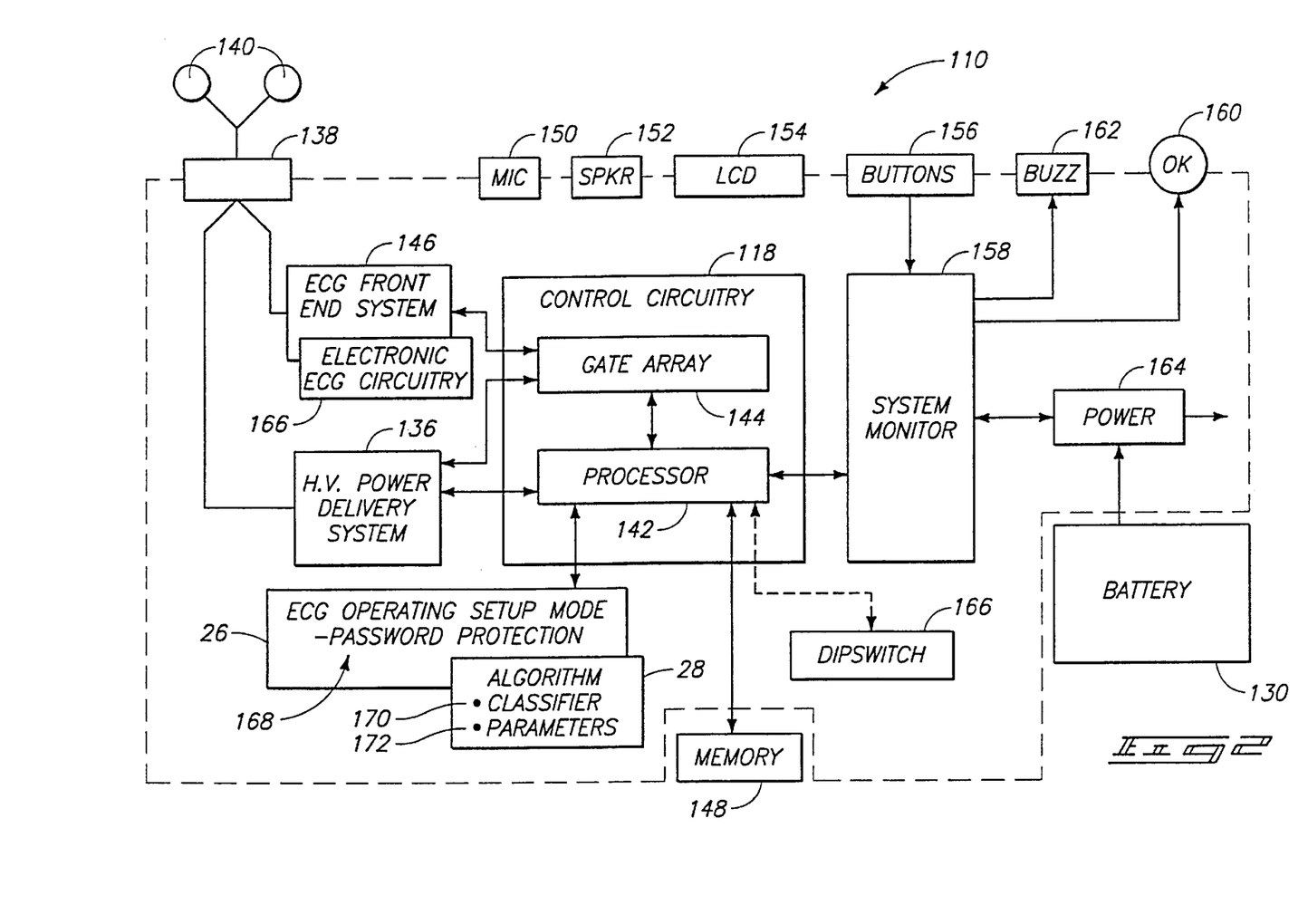
FIG. 2 is a schematic block diagram of a defibrillator implementing this invention.

FIG. 2 is a block diagram showing one preferred configuration for the defibrillator of this invention. As shown in FIG. 2, external defibrillator 110 has a power source such as a removable battery 130, a controller such as control circuitry 118, and a high-voltage power delivery system 136, including a capacitor or capacitor bank and appropriate switches (not shown). Power source 130, control circuitry 118, and high-voltage power delivery system 136 are configured and operatively coupled to deliver a pulse of electrical energy to an electrode connector, or interface, 138 and then to a patient via electrodes 140. A processor 142 of control circuitry 118 controls delivery of an electrical pulse to a patient.

An electrocardiogram (ECG) front-end system 146 acquires and preprocesses patient ECG signals via electrodes 140. System 146 also includes electrocardiogram (ECG) electronic circuitry 166. Such preprocessed signals are sent to processor 142 (here a central processing unit) via a system gate array 144. System gate array 144 comprises a custom Application-Specific Integrated Circuit (ASIC) that integrates many of the defibrillator's functions, such as display control and many of the instrument control functions, thereby minimizing the number of parts and freeing up main processor time for use in other tasks. Gate array 144 can be replaced by discrete logic and/or another processor, as known in the art.

As shown in FIG. 2, defibrillator 110 has a memory device 148 provided in the form of a removable PCMCIA card. Additionally, defibrillator 110 has a microphone 150, a speaker 152, a liquid crystal display (LCD) panel 154, and illuminated push-button controls, or buttons 156.

Defibrillator 110 also includes a system monitor 158 operative to mediate self-testing functions provided within the defibrillator by watching for scheduled test times and unscheduled power-on events. A test signal is generated periodically at scheduled times and in response to specific events by system monitor 158. In conjunction therewith, system monitor 158 operates a fail-safe defibrillator status indicator via display 160. System monitor 158 communicates test signals to processor 142 via a communication channel, and processor 142 controls and gathers information from tested defibrillator components via other communications channels, some of which pass through system gate array 144. A buzzer, or audible speaker, 162 is further provided for indicating status via system monitor 158.

Furthermore, system monitor 158 is coupled via battery 130 by way of a general power supply 164 operative to power selected components within defibrillator 110.

As shown in FIG. 2, processor 142 of control circuitry 118 is used to implement an electrocardiogram (ECG) operating setup mode 26. Setup mode 26 includes a password protection system 168, e.g., a software-based security password requiring the user to input a security code or password prior to entering the setup mode. The user can enter setup mode 26 by providing a secured password protection system 168 in order to access the algorithm 28. Algorithm 28 includes a classifier 170 which associates one or more parameters 172 that characterize patient heart rhythm.

According to one implementation, classifier 170 comprises a simple algebraic equation, $Z=A*P1+B*P2+C*P3$, that combines detected parameter values (P1, P2, P3) via a simple mathematical operator such as addition and subtraction. Such algebraic equation is compared with a threshold value in order to determine whether or not defibrillator 110 should be armed so as to provide the user with an ability to deliver a shock to a patient by pressing an operator button (such as button 97 depicted in FIG. 4).

According to another implementation, classifier 170 comprises a polynomial equation formed by a plurality of parameters 172. For example, one parameter comprises a normalized value for detected heart rate (wherein heart rate can range from 30–300 beats per minute). Another parameter can be a normalized value for morphological stability of complexes found within a heart rhythm (i.e., the shape of the complex is represented by a numeric value). A third parameter comprises a normalized value for heart conduction properties. Accordingly, each parameter can be measured for a patient, with the parameter being normalized within a predefined range of values, and the above three parameters then being combined according to a simple polynomial equation so as to produce a specific resultant value. The resultant value from the polynomial equation is then compared to the predetermined range of output values; certain selected output values causing shock delivery to be enabled such that an operator can push a button and shock a patient as a result thereof. Other values will produce a determination that a "no-shock" condition exists, preventing delivery of a shock to a patient by an operator.

Yet another configuration for classifier 170 comprises a neural network wherein a plurality of parameters 172 provide the nodes within a neural network, each of such parameters being weighted with a specific coefficient that is determined based upon experiential data and training of the neural network. One such neural network comprises a single-layer discrete-time feedback network. Other neural network implementations are also acceptable.

It is understood that classifier 170 of FIG. 2 can be formed from any of a number of associated mathematical implementations, including mechanical calculators capable of enabling controlled access personnel to associate parameters in one of a number of manners such that classifier 170 will provide desired functionality for an intended operator that is expected to be found within a specific deployment environment. In this manner, defibrillator 110 can be deployed into any of a number of different operating environments having specific configured functionality deliverable to an operator having an expected level of training and/or skill. In this manner, the operator can be imparted with varying levels of discretionary user features (or functionality) when deciding whether to deliver a shock to a patient. Furthermore, a specific defibrillator 110 can be redeployed into different environments in a manner that enables reconfiguration so as to provide a different level of functionality and operator discretion when delivering a shock to a patient within a different deployment environment. For example, defibrillator 110 of FIG. 2 can be deployed into a first deployment environment where a physician is the expected operator. According to a second deployment environment, defibrillator 110 is configured with functionality suitable for a paramedic. According to a third deployment environment, defibrillator 110 is configured with functionality suitable for an emergency medical technician. According to a fourth deployment environment, defibrillator 110 is configured with functionality suitable for a flight attendant.

Figure 3:
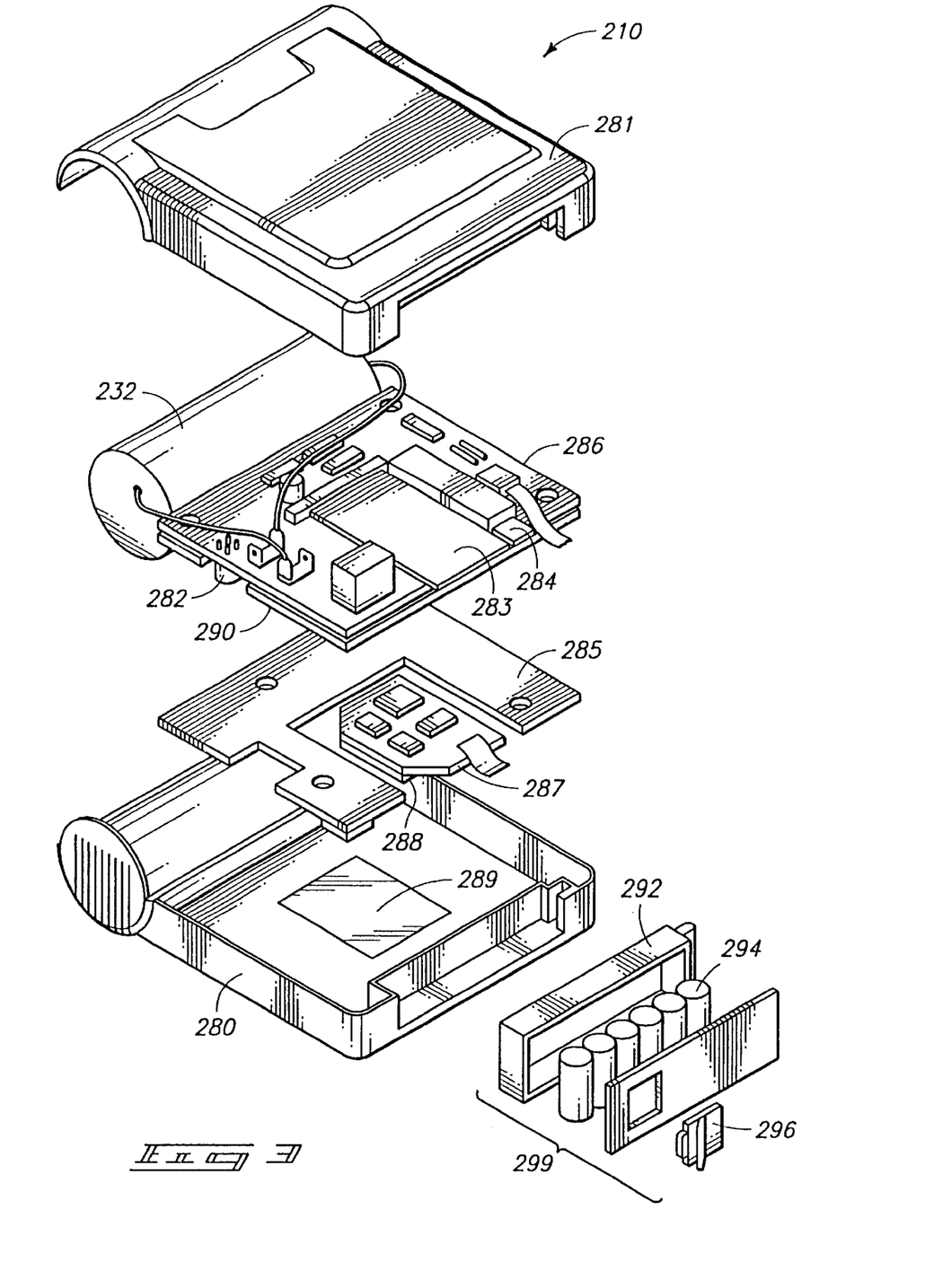
FIG. 3 is an exploded perspective view of the defibrillator shown in FIG. 2.

FIGS. 3 and 4 illustrate one implementation of the external defibrillator shown schematically in FIG. 2. Defibrillator 210 includes a molded two-part plastic housing formed from an upper case 280 and a lower case 281. A main printed circuit board (PC board) 286 supports a capacitor 232 (part of the high-voltage power delivery system 136 of FIG. 2), an electrode connector 282 (electrode interface 138 of FIG. 2), a PCMCIA memory card 283 (corresponding to memory device 148 of FIG. 2), and a PCMCIA memory card ejector mechanism 284. PCMCIA memory card 283 lies within a PCMCIA memory card slot 295 on PC board 286.

A keyboard PC board 285 and a display PC board 287 are disposed between main PC board 286 and upper case 280. Keyboard PC board 285 interfaces with the defibrillator's operator buttons 297 and 298 (the illuminated push-button control buttons 156 of FIG. 2), and display PC board 287 operates the defibrillator's LCD display 288 (element 154 of FIG. 2). A display window 289 is provided in upper case 280 for permitting display 288 to be seen by an operator.

A battery assembly 299 (corresponding to battery 130 of FIG. 2) consisting of a battery housing 292 and six lithium-manganese dioxide primary cells 294 is disposed in upper case 280 such that the batteries are provided in electrical contact with the capacitor charge circuits and other circuits of main PC board 286. Battery assembly 299 has a latching mechanism 296 operative for attaching and detaching the battery assembly to and from defibrillator 210.

Battery assembly 299 is located in front of PCMCIA memory card slot 295 so as to prevent a defibrillator operator or others from accessing PCMCIA card 283 while defibrillator 210 is powered up and operating. Such arrangement protects an operator and patient from accidental shocks and protects defibrillator 210 itself from damage caused by inadvertent removal of PCMCIA card 283 during operation.

Also illustrated in FIG. 3, an insulator 290 is disposed between main PC board 286 and display PC board 287. A sealing gasket (not shown) lines the edges between upper case 280 and lower case 281 when the housing is assembled.

As shown in FIGS. 2–4, a defibrillator is provided having features that are operable in a semi-automatic or an automatic mode. A semi-automatic mode may be entered by depressing on/off button 298, as shown in FIG. 4. After a power-on self-test (e.g., as described in U.S. patent application Ser. No. 08/240,272), the defibrillator displays an operational status on display 288, through window 289. If the defibrillator is operational, the defibrillator begins charging capacitor 232 and proceeds to electroanalysis.

Once electrodes have been attached, the attachment has been verified, and it has been determined that the defibrillator is operational, the configured defibrillator begins analyzing a patient's electrocardiogram (ECG) in order to make a "shock" or "no-shock" decision in a manner known in the art. In such state, the defibrillator displays an "analyzing" or similar message on display 288. The defibrillator may also analyze the quality of the ECG information that is being received, and will display a message such as "analyzing stopped" (possibly accompanied by a voice prompt) if a suspected motion artifact (or other artifact) appears in the ECG signal.

In the event the defibrillator makes three consecutive "no-shock" decisions according to an analysis protocol, the defibrillator displays "no shock advised" or a similar message on display 288 and continues a monitoring operation. If, however, the defibrillator makes a "shock" decision, it immediately completes charging of capacitor 232 and displays a message such as "prepare to shock". Such visual messages may also be accompanied by voice prompts. Additionally, the defibrillator preferably emits a tone during capacitor charging, with the pitch of the tone rising as the charging process nears completion.

Once capacitor 232 is fully charged, the defibrillator becomes armed. The defibrillator indicates such condition by illuminating shock button 297 and both visual and voice prompting "First, prepare to Shock—Stand Clear", then "Shock Advised—Press to Shock" or some similar messages. Additionally, a continuous tone alternates with the voice prompts to further notify an operator. An operator/user then delivers a shock to the patient by depressing shock button 297. After delivery of a shock, the defibrillator emits a "Shock Delivered" (or its equivalent) visual and/or voice prompt, then transitions to an analysis state.

During the process of charging, a user may disarm the defibrillator by depressing on/off button 298.

Additionally, the defibrillator display 288 is operative to show real time patient ECG waveforms, heart rate, number of shocks delivered, elapsed time, defibrillator condition (e.g., low battery warning), and any other relevant information. The defibrillator may also be able to display data from earlier uses in an "Event Review Mode". Similar defibrillator operations may also be provided for automatic and manual operation of the defibrillator.

According to this invention, the defibrillator's ability to make "shock" or "no-shock" decisions is based upon a specific configuration of the ECG front-end system 146 as realized by classifier 170 (of FIG. 2). In order to achieve such tailored result, an ECG operating setup mode 26 is implemented within control circuitry 118, via processor 142, to realize a desired configuration for distinguishing between definite shockable rhythms, definite non-shockable rhythms, and borderline rhythms that are clearly shockable or non-shockable, based upon the training and skill level of a particular operator found within a particular deployment environment. More particularly, a configurable arrhythmia analysis algorithm 28 comprises a classifier 170 having parameters 172 that are configured in association via ECG operating setup program 26 by way of processor 142 to enable a manufacturer or product control individual to configure the defibrillator 110 for a particular intended use and environment.

For the simplest case, an adjustment option involves adjusting parameters 172 of classifier 170 which would allow for algorithm 28 to be configured for a specific operating environment. For example, one configuration can be provided for skilled operators and a different one can be provided for minimally-skilled operators. Preferably, algorithm 28 is designed from a standard set of ECG measures that are compared or combined in conjunction with a classifier which mathematically associates the measures (of each parameter) to produce a "shock/no-shock" decision. Accordingly, different specific configurations of algorithm 28 can be achieved by modifying the parameters for such classifier, using the same set of standard ECG measures for all configurations.

Accordingly, it is possible to provide for a plurality of different configurations for one defibrillator such that operators having varying degrees of identifiable skill level can be provided with a specially configured defibrillator having a pre-configured ECG capability for implementing arrhythmia analysis that enables functionality that is related to the skill level and training of the intended operator or user.

Figure 5:
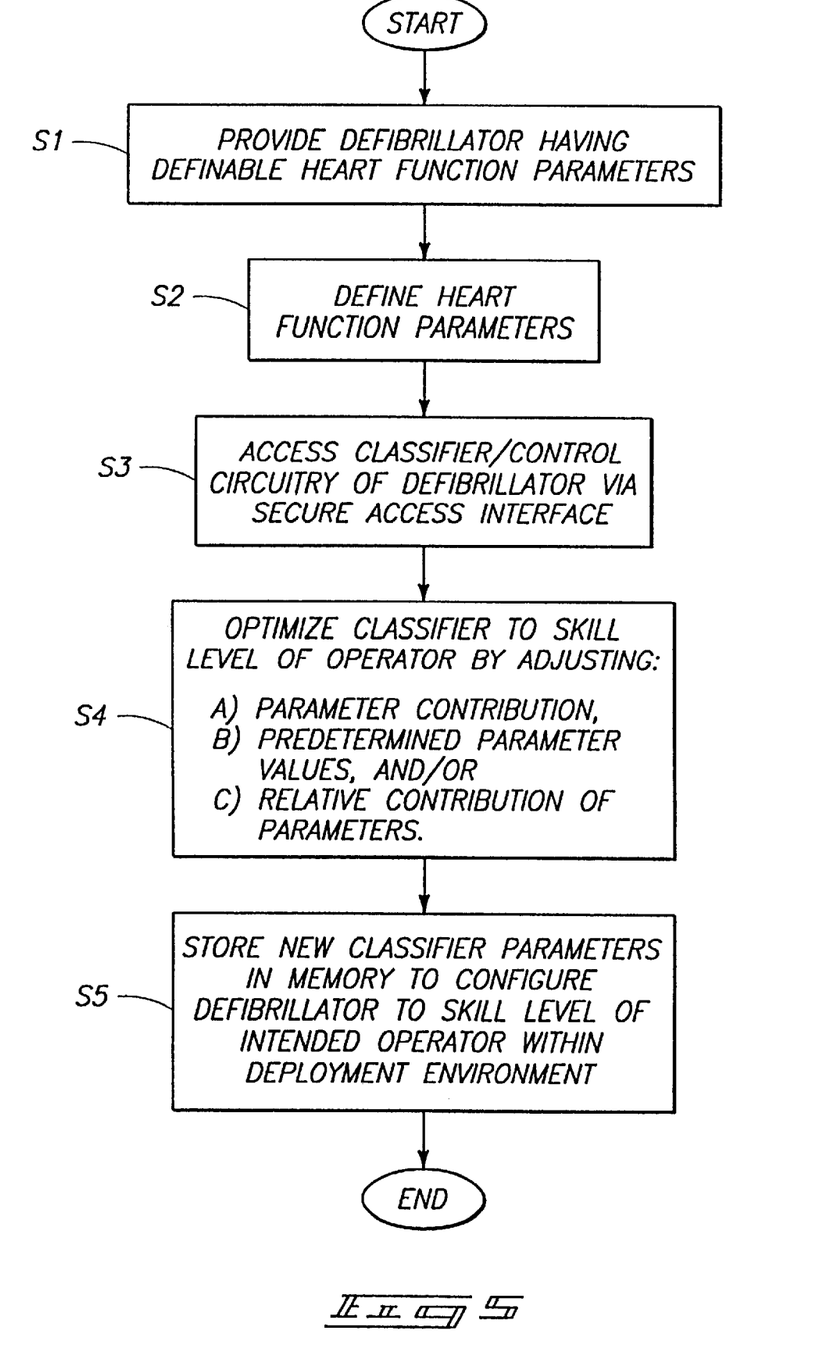
FIG. 5 is a flowchart illustrating one technique for reconfiguring electrocardiogram (ECG) functionality within an automated defibrillator.

FIG. 5 details a general implementation of the invention wherein a method and an apparatus are provided for configuring arrhythmia analysis and shock delivery by configuring an ECG signal processor or circuitry of a defibrillator to deliver functionality that matches the skill level of an intended operator found within an intended deployment environment. In one embodiment, secure access is provided to the software within a defibrillator such that a control person or manufacturer can configure the defibrillator such that the resulting defibrillator functionality is optimized between sensitivity and specificity so as to best match the training and skill level for an intended operator.

In another embodiment, a dip switch 166 (shown optionally in FIG. 2) is provided within a secure location inside the housing of a defibrillator, away from the access of normal users or operators. A control person having restricted access can open the housing to enable selective setting of the dip switch which corresponds with configuring software and/or circuitry within the defibrillator so as to optimize the sensitivity and specificity of the ECG signal processing functionality within the defibrillator. Even further alternative implementations use software code to adjust control circuitry within the defibrillator such that desired parameter values are adjusted so as to modify a classifier that reconfigures ECG and/or shock-delivery functionality within the defibrillator. One embodiment is illustrated via a flowchart that is implemented on a processor in FIG. 5 as described below.

In Step S1, a defibrillator is provided to a manufacturer, a trained technician, or personnel having controlled access. The controlled access personnel can be an individual having a physical or software access key that enables secure access to a classifier having definable heart function parameters which combine to produce a "shock/no-shock" decision for the defibrillator. For example, the nodes (or parameters) of a neural network can be adjusted by a medical devices distributor who maintains/services the defibrillator.

In Step S2, a set of specific heart function parameters are defined, each characterizing heart rhythms of a patient being detected by a defibrillator. Additionally, a mapping is provided between detected heart parameter values and a known set of predetermined values for purposes of comparing the detected parameter value with a known heart rhythm.

In Step S3, a classifier (or control circuitry) of the defibrillator is accessed by a manufacturer or secure access personnel via a secure access interface such as a mechanical or software access key. One exemplary technique entails utilization of a password code that is prompted when running ECG operating setup mode 26 (of FIG. 2). A secure access personnel provides a security password which enables access and modification of parameters defining the classifier. An optional technique entails utilization of a physical key which enables secure access to such classifier.

In Step S4, the classifier is optimized to the skill level of an operator by adjusting one or more of: (a) the weighted contribution of each specific parameter; (b) acceptable predetermined parameter values that represent a specific measurable quantity indicating a specific heart rhythm feature; and (c) the relative contribution of one parameter with respect to other parameters. Additionally, the skill level of an intended operator within an intended deployment environment is determined as described below with reference to the sub-routine depicted in FIG. 6. Based upon the determined skill level of an intended operator, the classifier is adjusted by adjusting features (a)–(c), as noted above, in the manner best suited for the intended operator.

In Step S5, classifier parameters are set and stored by secure access personnel in order to configure the ECG arrhythmia analysis functionality of the defibrillator for the intended operator. More particularly, ECG functionality of the defibrillator is made operative so as to best match the skill level of an intended operator present within an intended deployment environment. According to one implementation, the new classifier parameters are stored within memory 148 (of FIG. 2). According to another implementation, such new classifier parameters are stored within memory of control circuitry 118, such as within gate array 144.

Figure 6:
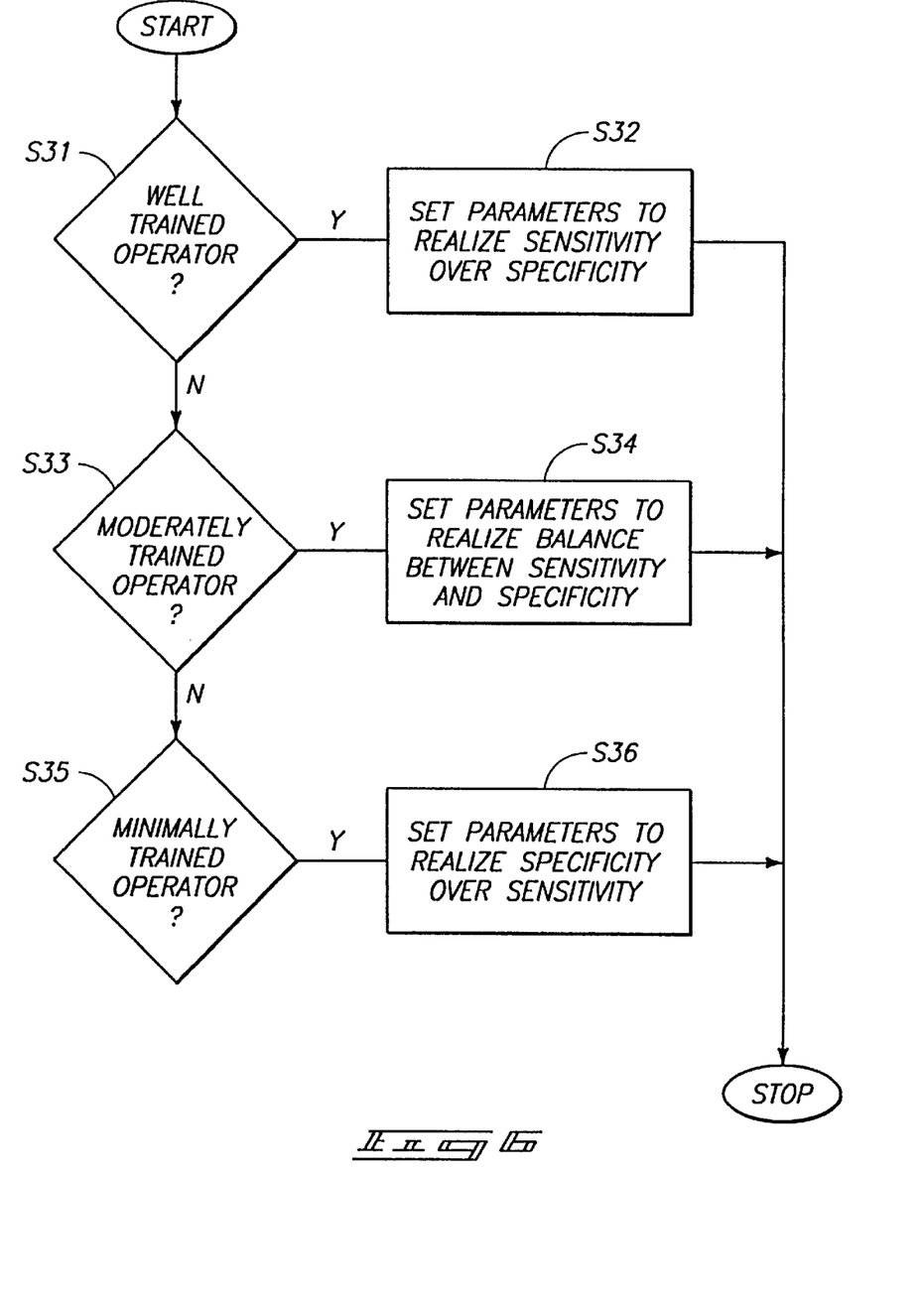
FIG. 6 is a flowchart of a sub-routine for determining the skill level of an intended operator.

FIG. 6 illustrates a sub-routine implementation for determining the intended operator used in Step S3 (of FIG. 5).

In Step S31, processor 142 (of FIG. 2) questions whether an intended operator is expected to be well trained. If the intended operator is well trained, the process proceeds to Step S32. If not, the process proceeds to Step S33.

In Step S32, the processor sets the classifier parameters so as to realize "sensitivity" over "specificity". Details of such emphasis for realizing "sensitivity" over "specificity" are described below with reference to FIG. 7. After performing Step S32, the process stops and returns to Step S4 in FIG. 5.

In Step S33, the processor questions whether the intended operator is moderately trained. If the intended operator is moderately trained, the process proceeds to Step S34. If not, the process proceeds to Step S35.

In Step S34, the processor sets the classifier parameters to realize a balance between "sensitivity" and "specificity". After performing Step S34, the process proceeds back to Step S4 in FIG. 5.

In Step S35, the processor determines whether the intended operator is minimally trained. After performing Step S35, the process proceeds to Step S36.

In Step S36, the processor sets the classifier parameters to realize "specificity" over "sensitivity". After performing Step S36, the process proceeds back to Step S4 of FIG. 5.

Figure 7:
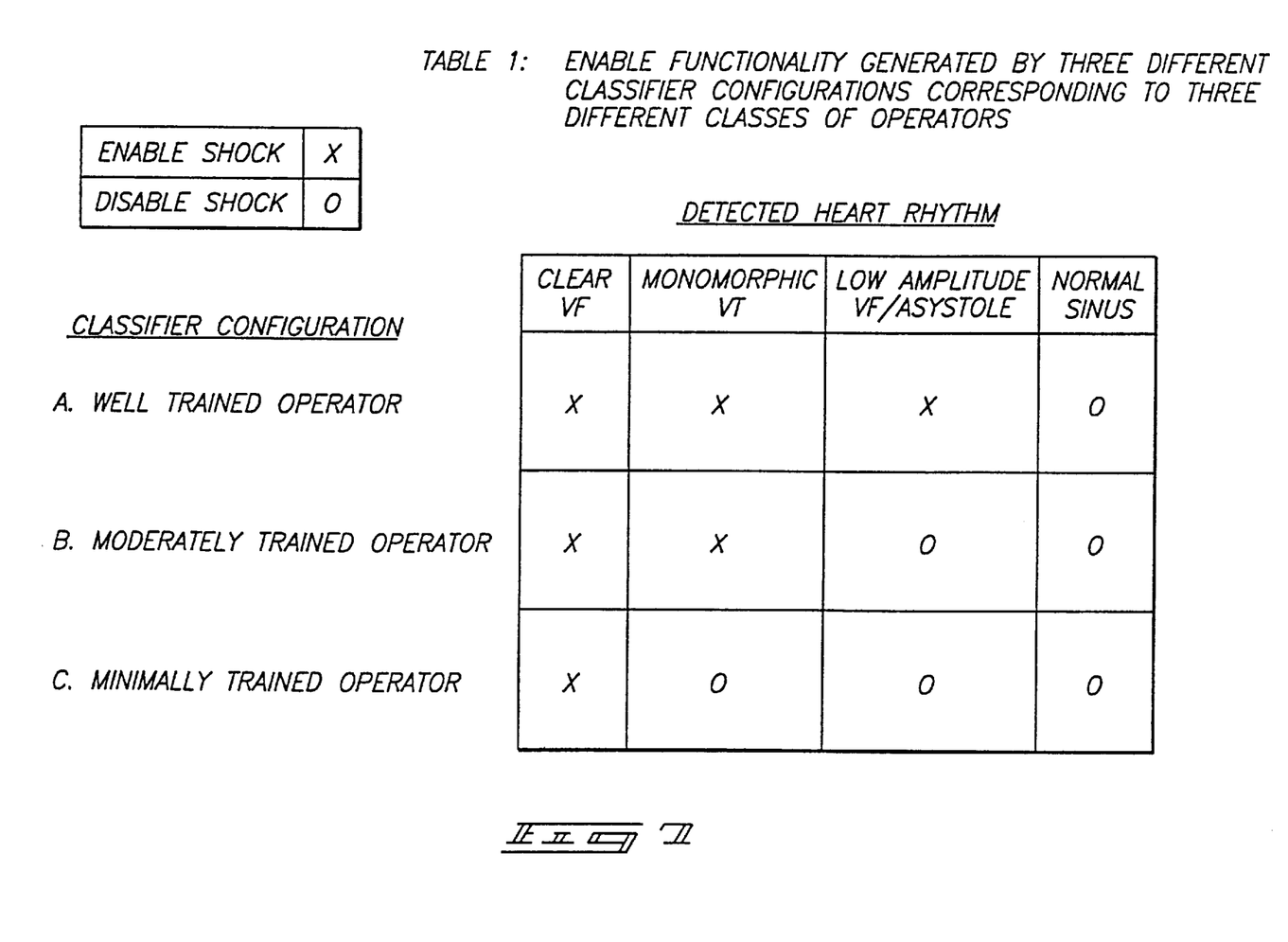
FIG. 7 is a table illustrating tailored functionality generated by adjusting parameters utilized to realize three different exemplary predetermined configurations of sensitivity and specificity for an ECG arrhythmia analysis algorithm capable of being configured for an operator having a predetermined skill level and amount of training.
Figure 11:
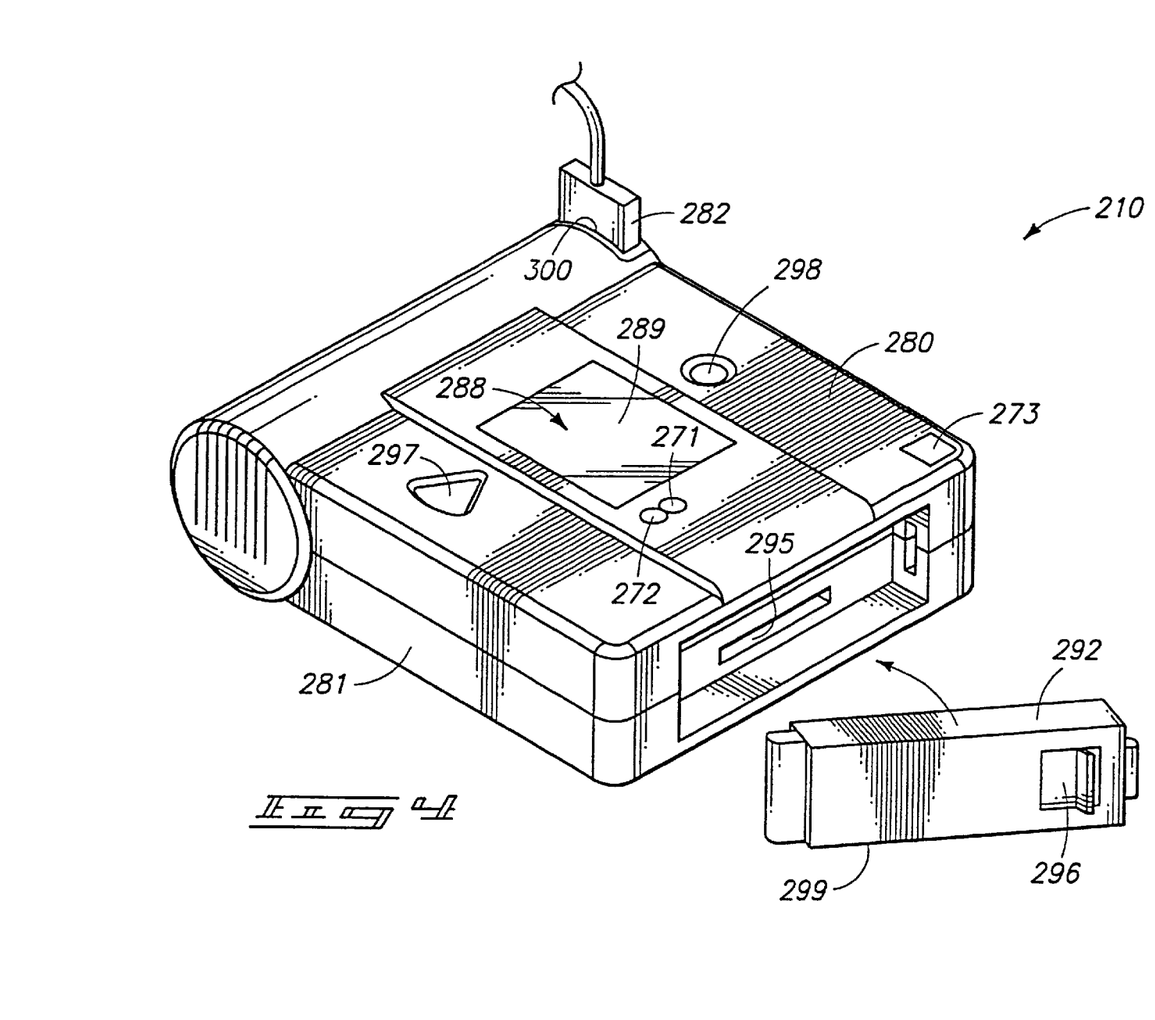

FIG. 7 illustrates a table representing one set of detected rhythms as they are classified by three distinct classifier configurations realized by a defibrillator of this invention. The classifier is shown to realize an identifying configuration for an ECG arrhythmia analysis algorithm having three levels of intended operators. More particularly, three classes of intended operators comprise "well-trained operators", "moderately-trained operators", and "minimally-trained operators". Table 1 of FIG. 7 illustrates one example of four identifiable heart rhythms that are capable of being identified with any of a number of presently understood ECG signal analyzers that produce different functionality to operators having different skill levels/training; namely, "Clear Ventricular Fibrillation", "Monomorphic Ventricular Tachycardia", "Low-Amplitude Ventricular Fibrillation (VF/asystole)", and "Normal Sinus Activity".

According to the depiction in Table 1, a parameter designated with "X" indicates that a "shock" decision should be produced. Likewise, a parameter "O" indicates a "no-shock" decision.

According to the depiction in Table 1, controlled access personnel reconfigure the defibrillator of this invention such that shock delivery is tailored for specific detected heart rhythms based upon the configuration of a classifier according to the level of training and/or skill level of an operator. As shown in Table 1 of FIG. 7, imparted functionality is depicted with a "X" indicating that a "shock" decision is produced which enables an operator to trigger a shock to a patient. Likewise, a parameter "O" indicates a "no-shock" decision has been generated by the defibrillator indicating that shock delivery cannot be imparted by an operator.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A defibrillator, comprising:
    a front-end circuit operable to receive a parameter indicative of a patient's heart function;
    a controller coupled to the front-end circuit and operable to determine whether an operator should provide an electrical shock to the patient based on the parameter and an expected level of skill the operator has in treating the patient;
    a housing; and
    secure means disposed within the housing for adjusting the expected level of the operator's skill.

2. The defibrillator of claim 1, further comprising a pair of electrodes operable to apply the electrical shock to the patient.

3. The defibrillator of claim 1 wherein the controller is configurable according to the expected level of the operator's skill.

4. The defibrillator of claim 1 wherein the controller is reconfigurable to accommodate a change in the expected level of the operator's skill.

5. The defibrillator of claim 1, further comprising:
    a shock circuit coupled to the controller and operable to deliver the electrical shock to the patient; and
    wherein the controller is operable to enable the shock circuit in response to the parameter and the expected level of the operator's skill.

6. The defibrillator of claim 1, further comprising an interface coupled to the controller and operable to allow one to configure the controller according to the expected level of the operator's skill.

7. The defibrillator of claim 1, further comprising an interface coupled to the controller and operable to allow one to reconfigure the controller to accommodate a change in the expected level of the operator's skill.

8. A defibrillator, comprising:
    a shock circuit operable to deliver an electrical shock to a patient in response to an instruction from an operator having an expected level of skill in treating the patient;
    a controller coupled to the shock circuit and operable to exercise a level of control over the shock circuit, the level of control related to the expected level of the operator's skill;
    a housing; and
    secure means disposed within the housing for adjusting the expected level of the operator's skill.

9. The defibrillator of claim 8, further comprising a pair of electrodes operable to apply the electrical shock from the shock circuit to the patient.

10. The defibrillator of claim 8 wherein the level of control exercised by the controller is configurable to relate to the expected level of the operator's skill.

11. The defibrillator of claim 8 wherein the level of control exercised by the controller is reconfigurable to accommodate a change in the expected level of the operator's skill.

12. The defibrillator of claim 8 wherein the level of control that the controller exercises over the shock circuit comprises a level of enablement.

13. The defibrillator of claim 8, further comprising:
a front-end circuit coupled to the controller and operable to receive a parameter indicative of a patient's heart function; and
wherein the controller is operable to control the shock circuit in response to the parameter and in accordance with the level of control corresponding to the expected level of the operator's skill.

14. The defibrillator of claim 8 wherein the level of control exercised by the controller is configurable to increase as the expected level of the operator's skill decreases.

15. The defibrillator of claim 8, further comprising an interface coupled to the controller and operable to allow one to configure the level of control exercised by the controller to relate to the expected level of the operator's skill and to reconfigure the controller to accommodate a change in the expected level of the operator's skill.

16. A defibrillator, comprising:
a front-end circuit operable to receive a parameter indicative of a patient's heart function; and
a controller coupled to the front-end circuit and operable to determine whether an electrical shock should be provided to the patient, the controller operable to make this determination by operating on the parameter with a configurable algorithm.

17. The defibrillator of claim 16 wherein the algorithm is reconfigurable.

18. The defibrillator of claim 16 wherein:
the controller is operable to determine whether an operator should provide the electrical shock to the patient, the operator having an expected level of skill in treating the patient; and
the algorithm is configurable to correspond with the expected level of the operator's skill.

19. The defibrillator of claim 16 wherein:
the controller is operable to determine whether an operator should provide the electrical shock to the patient, the operator having an expected level of skill in treating the patient;
the algorithm is configurable to correspond with the expected level of the operator's skill; and
the algorithm is reconfigurable to accommodate a change in the expected level of the operator's skill.

20. The defibrillator of claim 16 wherein:
the controller is operable to determine whether a first operator should provide the electrical shock to the patient, the first operator having a first expected level of skill in treating the patient;
the algorithm is configurable to correspond with the first expected level of skill;
the controller is operable to determine whether a second operator should provide the electrical shock to the patient, the second operator having a second expected level of skill in treating the patient, the second expected level of skill being different than the first expected level of skill; and
the algorithm is reconfigurable to correspond to the second expected level of skill.

21. The defibrillator of claim 16, further comprising an interface coupled to the controller and operable to allow one to configure and reconfigure the algorithm.

22. A method, comprising:
receiving a parameter having a parameter value that corresponds to a patient's heart function; and
determining whether an operator should provide an electrical shock to the patient based on the parameter value and an expected level of the operator's medical training.

23. The method of claim 22, further comprising instructing the operator to provide the electrical shock to the patient if it is determined that the operator should provide the electrical shock.

24. A method, comprising:
providing a defibrillator having a housing and secure means disposed within the housing for adjusting an expected level of operator skill;
analyzing a patient's heart function using the defibrillator; and
controlling defibrillating-shock treatment of the patient with a degree of control that is related to a caregivers' expected level of skill in treating a heart ailment.

25. The method of claim 24, further comprising adjusting the degree of control to correspond to the caregiver's expected level of skill.

26. The method of claim 24, further comprising:
expecting the caregiver to have a first level of skill in treating a heart ailment;
anticipating a change in the caregiver's expected level of skill from the first level to a second level; and
adjusting the degree of control to correspond to the second level of skill.

27. The method of claim 24 wherein the controlling comprises enabling defibrillating-shock treatment of the patient with a degree of control that is related to the caregivers' expected level of skill in treating a heart ailment.

28. The method of claim 24 wherein the controlling comprises controlling the defibrillating-shock treatment of the patient with a degree of control that is inversely proportional to the caregivers' expected level of skill in treating a heart ailment.

29. The method of claim 24 wherein the controlling comprises controlling the defibrillating-shock treatment of the patient with a degree of control that is related to the caregivers' expected level of skill and to an analysis of the patient's heart function.

30. A method, comprising:
receiving a parameter having a value that is indicative of a patient's heart function; and
determining whether the patient should be shocked by operating on the parameter with a configurable algorithm.

31. The method of claim 30, further comprising reconfiguring the algorithm.

32. The method of claim 30, further comprising configuring the algorithm in relation to a rescuer's expected level of skill in treating the patient.

33. The method of claim 30, further comprising:
configuring the algorithm in relation to a rescuer's expected level of skill in treating the patient; and
reconfiguring the algorithm in response to a change in the rescuer's expected level of skill.

34. The method of claim 30, further comprising:
configuring the algorithm in relation to a first rescuer's expected level of skill in treating the patient; and
reconfiguring the algorithm in relation to a second rescuer's expected level of skill in treating the patient.

* * * * *